(12) United States Patent
Naidu et al.

(10) Patent No.: US 11,291,802 B2
(45) Date of Patent: Apr. 5, 2022

(54) FLUID STORAGE UNIT, SYSTEMS, AND METHODS FOR CATHETER PRIMING

(71) Applicant: Becton, Dickinson and Company

(72) Inventors: Jithendra Kumar Sathyanarayana Naidu, Woodlands (SG); Mum Pew Ng, Tampines (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 178 days.

(21) Appl. No.: 16/150,902

(22) Filed: Oct. 3, 2018

(65) Prior Publication Data

US 2019/0105464 A1    Apr. 11, 2019

Related U.S. Application Data

(60) Provisional application No. 62/569,833, filed on Oct. 9, 2017.

(51) Int. Cl.
*A61M 25/06* (2006.01)
*A61M 39/22* (2006.01)
(Continued)

(52) U.S. Cl.
CPC .......... *A61M 25/0606* (2013.01); *A61J 1/067* (2013.01); *A61J 1/10* (2013.01);
(Continued)

(58) Field of Classification Search
CPC .......... A61M 25/0026; A61M 25/0612; A61M 25/0068; A61M 25/0097; A61M 25/00;
(Continued)

(56) References Cited

U.S. PATENT DOCUMENTS 4,683,916 A * 8/1987 Raines .................. A61M 39/26
                                                                    137/854
4,798,605 A * 1/1989 Steiner ...................... A61J 1/10
                                                                    604/411
(Continued)

FOREIGN PATENT DOCUMENTS

CN        106620995 A    5/2017
WO        2017/074684    5/2017

OTHER PUBLICATIONS

Teresa Bergen, Gynecologic Laparoscopy, Nov. 28, 2017, Healthline Media. (Year: 2017).*
(Continued)

*Primary Examiner* — Jenna Zhang
(74) *Attorney, Agent, or Firm* — Kirton Mcconkie; Whitney Blair; Kevin Stinger

(57) ABSTRACT

A catheter system may include a catheter assembly, a fluid storage unit, and fluid. The catheter assembly may include a catheter hub, a catheter, an extension tube, and an adapter. The catheter hub may include a distal end, a proximal end, a lumen extending between the distal end and the proximal end, and a side port. The catheter may extend distally from the distal end of the catheter hub. A distal end of the extension tube may be coupled to the side port. The adapter may be coupled to a proximal end of the extension tube. The fluid storage unit may be coupled to the adapter and may include a reservoir, a barrier, and an actuator. The fluid may be disposed within the reservoir. In response to breach of the barrier by the actuator, the reservoir may be in fluid communication with the lumen of the catheter hub.

16 Claims, 5 Drawing Sheets

(51) Int. Cl.
  *A61M 25/00* (2006.01)
  *A61J 1/14* (2006.01)
  *A61M 5/142* (2006.01)
  *A61J 1/10* (2006.01)
  *A61J 1/06* (2006.01)
  *A61M 25/01* (2006.01)
  *A61M 39/06* (2006.01)
  *A61M 5/24* (2006.01)
  *A61M 5/152* (2006.01)
  *A61M 5/158* (2006.01)
  *A61M 39/00* (2006.01)

(52) U.S. Cl.
  CPC .......... *A61J 1/1406* (2013.01); *A61M 5/1428* (2013.01); *A61M 25/0026* (2013.01); *A61M 25/0068* (2013.01); *A61M 25/0097* (2013.01); *A61M 39/22* (2013.01); *A61M 5/152* (2013.01); *A61M 5/158* (2013.01); *A61M 5/2425* (2013.01); *A61M 2005/1587* (2013.01); *A61M 2005/247* (2013.01); *A61M 2025/0018* (2013.01); *A61M 2025/018* (2013.01); *A61M 2039/0018* (2013.01); *A61M 2039/062* (2013.01); *A61M 2205/123* (2013.01)

(58) Field of Classification Search
  CPC .......... A61M 2005/14284; A61M 2005/1587; A61M 2005/247; A61M 2025/018; A61M 31/00; A61M 2039/0018; A61M 3/0262; A61M 5/1428; A61M 5/2425; A61M 2039/0081; A61J 1/067; A61J 1/1406
  See application file for complete search history.

(56) References Cited

U.S. PATENT DOCUMENTS

| | | | | |
|---|---|---|---|---|
| 5,505,707 | A * | 4/1996 | Manzie | A61M 3/0262 604/131 |
| 5,817,082 | A * | 10/1998 | Niedospial, Jr | B65D 51/227 604/414 |
| 6,189,580 | B1 * | 2/2001 | Thibault | A61J 1/2096 141/25 |
| 7,998,113 | B2 | 8/2011 | Swisher | |
| 10,492,992 | B1 * | 12/2019 | Cogley | A61J 1/2093 |
| 2008/0029540 | A1 * | 2/2008 | Johnson | B67B 7/26 222/83 |
| 2009/0270815 | A1 | 10/2009 | Stamp et al. | |
| 2011/0301572 | A1 * | 12/2011 | Vlodaver | A61M 31/00 604/514 |
| 2012/0097705 | A1 * | 4/2012 | Py | B67B 7/24 222/83 |
| 2014/0309551 | A1 * | 10/2014 | Burkholz | A61B 5/157 600/573 |
| 2016/0243347 | A1 * | 8/2016 | Geiger | A61M 39/24 |
| 2017/0119953 | A1 * | 5/2017 | Wen | A61B 90/70 |
| 2018/0155091 | A1 * | 6/2018 | Cafaro | A61J 1/1406 |

OTHER PUBLICATIONS

"Laparoscope." Merriam-Webster.com Dictionary, Merriam-Webster, https://www.merriam-webster.com/dictionary/laparoscope. (Year: 2020).*

* cited by examiner

FLUID STORAGE UNIT, SYSTEMS, AND METHODS FOR CATHETER PRIMING

RELATED APPLICATIONS

This application claims the benefit of U.S. Provisional Patent Application No. 62/569,833, filed Oct. 9, 2017, entitled FLUID STORAGE UNIT, SYSTEMS, AND METHODS FOR CATHETER PRIMING, of which is incorporated herein in its entirety.

BACKGROUND OF THE INVENTION

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient. In some instances, catheters and attached tubing sets that are used for fluid infusion may be primed prior to insertion into vasculature of the patient to remove air. If air bubbles are allowed to enter the vasculature of the patient, an embolism may form, which may cause serious injury to the patient.

BRIEF SUMMARY OF THE INVENTION

The present disclosure relates generally to a fluid storage unit and related systems and methods. In some embodiments, the fluid storage unit may facilitate priming of a catheter assembly, which may prevent use of a pre-filled syringe or connection to an IV drip chamber to prime the catheter assembly. In some embodiments, the catheter assembly may include an IV catheter assembly. In some embodiments, the fluid storage unit may be activated to release fluid within the fluid storage unit and facilitate priming of the catheter assembly prior to catheterization or insertion of the catheter assembly into vasculature of the patient.

In some embodiments, a catheter system may include the catheter assembly, which may include a catheter hub. In some embodiments, the catheter hub may include a distal end, a proximal end, and a lumen extending between the distal end and the proximal end. In some embodiments, the catheter hub may include a side port.

In some embodiments, the catheter assembly may include a catheter, which may extend distally from the distal end of the catheter hub. In some embodiments, the catheter assembly may include an extension tube, which may include a distal end and a proximal end. In some embodiments, the distal end of the extension tube may be coupled to the side port.

In some embodiments, the catheter assembly may include an adapter coupled to the proximal end of the extension tube. In some embodiments, the adapter may include a Y-adapter or another suitable adapter. In some embodiments, the catheter system may include the fluid storage unit. In some embodiments, the fluid storage unit may be coupled to the adapter. In some embodiments, the fluid storage unit may include one or more of the following: a reservoir, a barrier, and an actuator. In some embodiments, in response to breach of the barrier by the actuator, the reservoir may be in fluid communication with the lumen of the catheter hub. In some embodiments, the catheter system may include the fluid disposed within the reservoir, which may be used for priming of the catheter assembly.

In some embodiments, in response to breach of the barrier by the actuator and/or squeezing of the fluid storage unit, the fluid may flow from the reservoir into the lumen of the catheter hub. In these and other embodiments, the fluid storage unit may be compressible towards an axis of the fluid storage unit aligned with the actuator and/or the fluid storage unit may be compressible towards an axis of the fluid storage unit perpendicular to the actuator. In some embodiments, the barrier may be breached by the actuator in response to a proximal portion of the fluid storage unit and a distal end of the fluid storage unit being brought closer together. In some embodiments, the proximal portion of the fluid storage unit and the distal end of the fluid storage unit may brought closer together in response to the proximal portion of the fluid storage unit being pushed towards the adapter and/or the adapter being pushed towards the proximal portion of the fluid storage unit.

In some embodiments, the distal end of the fluid storage unit may include a luer adapter, which may allow the distal end of the fluid storage unit to be coupled to the adapter. In some embodiments, the actuator may include a hollow spike. In some embodiments, the barrier may include a septum. In some embodiments, the barrier may include a membrane, which may be hydrophobic. In some embodiments, the hydrophobicity of the membrane may prevent the fluid from leaking out of the reservoir.

In some embodiments, a method may include providing the catheter system. In some embodiments, the method may include breaching the barrier with the actuator such that the reservoir is in fluid communication with the lumen of the catheter hub. In some embodiments, the method may include squeezing the fluid storage unit such that the fluid flows from the reservoir into the lumen of the catheter hub. In some embodiments, breaching the barrier with the actuator may include bringing a proximal portion of the fluid storage unit and a distal end of the fluid storage unit closer together.

It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION OF THE INVENTION

The present disclosure relates generally to a fluid storage unit and related systems and methods. In some embodiments, the fluid storage unit may facilitate priming of a catheter assembly, which may prevent use of a pre-filled syringe or connection to an IV drip chamber to prime the catheter assembly.

Figure 1:
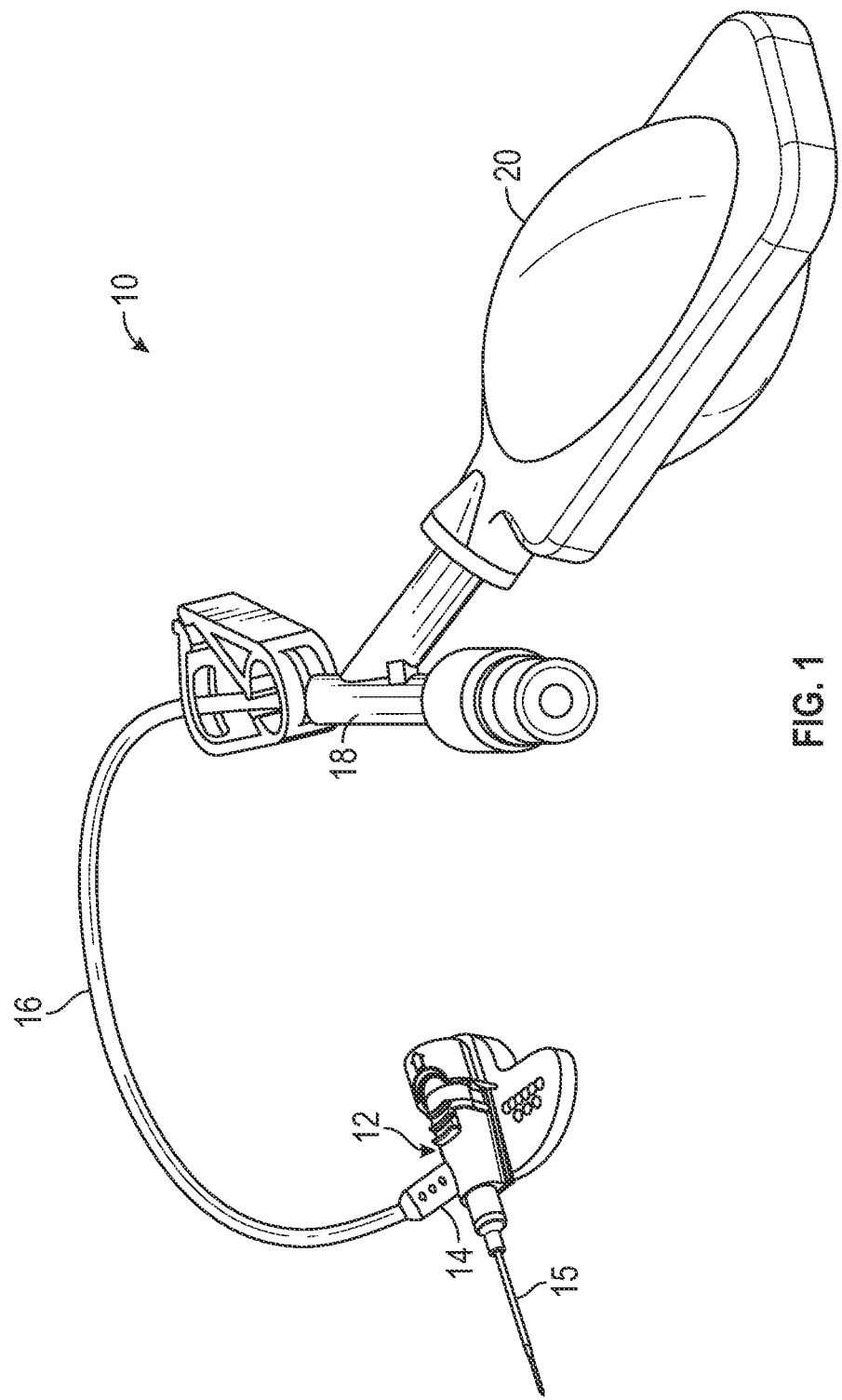
FIG. 1 is an upper perspective view of an example catheter system, according to some embodiments.

Referring now to FIG. 1, in some embodiments, a catheter system 10 may include a catheter assembly, which may include a catheter hub 12. In some embodiments, the catheter hub 12 may include a distal end, a proximal end, and a lumen extending between the distal end and the proximal end. In some embodiments, the catheter hub 12 may include a side port 14.

As used in the present disclosure, the terms "proximal" and "distal" may refer to a direction closer to and away from, respectively, a clinician who would place the catheter system into contact with a patient. For example, an end of the catheter system 10 first touching the body of the patient during insertion would be a distal end of the catheter system 10, while an opposite end of the catheter system 10 would be a proximal end of the catheter system 10.

In some embodiments, the catheter assembly may include a catheter 15, which may be secured within and/or extend distally from the distal end of the catheter hub 12. In some embodiments, the catheter assembly may include a peripheral IV catheter assembly. In some embodiments, the catheter assembly may include a closed IV catheter assembly, such as, for example, the Becton Dickinson NEXIVA™ Closed IV Catheter System or the Becton Dickinson NEXIVA™ DIFFUSICS™ Closed IV Catheter System. In these and other embodiments, the catheter assembly may include an extension tube 16, which may include a distal end and a proximal end. In some embodiments, the distal end of the extension tube may be coupled to the side port 14. In some embodiments, the catheter assembly may include another type of catheter assembly, such as, for example, a non-integrated catheter assembly or a catheter assembly without the extension tube 16.

In some embodiments, the catheter assembly may include an adapter 18, which may be coupled to the proximal end of the extension tube 16. In some embodiments, the adapter 18 may include a Y-adapter or another suitable adapter.

In some embodiments, the catheter system 10 may include a fluid storage unit 20. In some embodiments, the fluid storage unit 20 may be activated to release fluid within the fluid storage unit 20 and may facilitate priming of the catheter assembly.

Figure 2A:
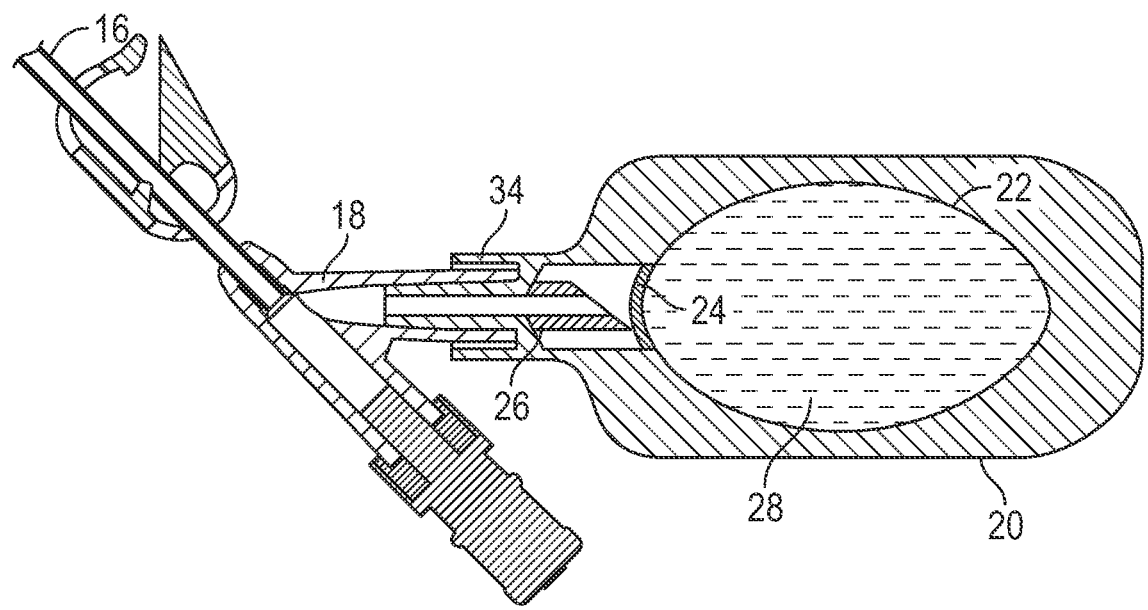
FIG. 2A is a cross-sectional view of an example fluid storage unit and example adapter of the catheter system of FIG. 1, according to some embodiments.
Figure 2B:
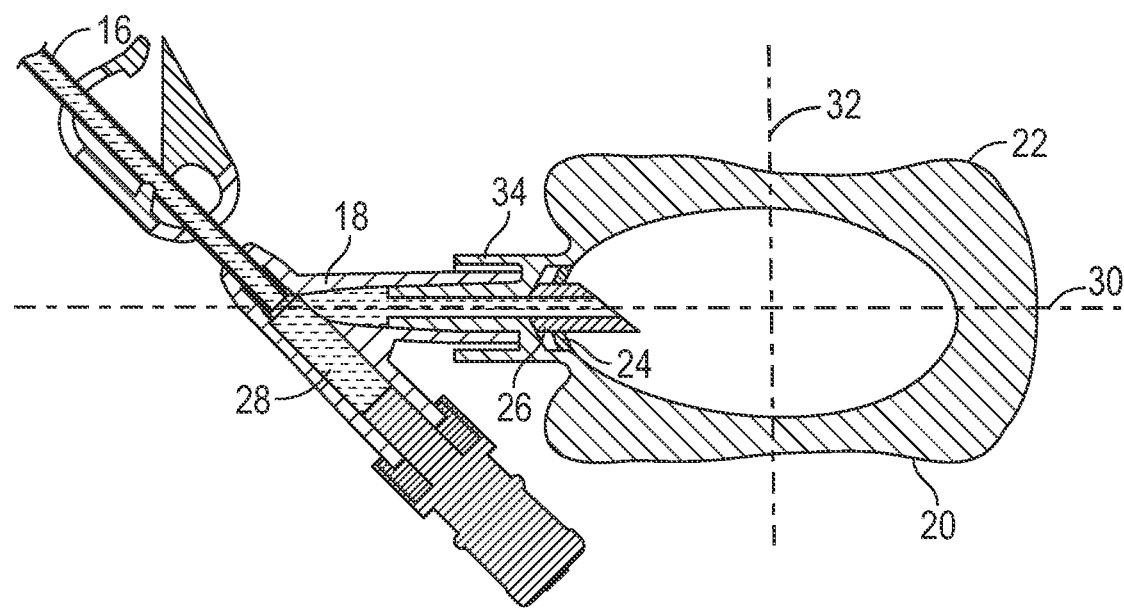
FIG. 2B is a cross-sectional view of the fluid storage unit and adapter of FIG. 2A, illustrating an example barrier breached by an example actuator, according to some embodiments.

In some embodiments, the fluid storage unit 20 may be coupled to the adapter 18. Referring now to FIGS. 2A-2B, in some embodiments, the fluid storage unit 20 may include one or more of the following: a reservoir 22, a barrier 24, and an actuator 26. In some embodiments, in response to breach of the barrier 24 by the actuator 26, the reservoir 22 may be in fluid communication with the lumen of the catheter hub 12. In some embodiments, the catheter system 10 may include fluid 28 disposed within the reservoir 22, which may be used for priming of the catheter assembly. In some embodiments, the fluid 28 may include a saline solution or another suitable priming fluid. In some embodiments, breaching the barrier 24 may include penetrating, puncturing, or another type of breach.

In some embodiments, priming of the catheter assembly may achieve a bubble-free fluid pathway of the catheter assembly. In some embodiments, the fluid pathway of the catheter assembly may include one or more of the following: the catheter 15, the catheter hub 12, the extension tube 16, and the adapter 18. In some embodiments, the priming of the catheter assembly may occur prior to catheterization or insertion of the catheter assembly into vasculature of a patient.

In some embodiments, in response to breach of the barrier 24 by the actuator 26 and squeezing of the fluid storage unit 20, the fluid 28 may flow from the reservoir 22 through an entirety of the fluid pathway of the catheter assembly and/or into the catheter assembly. Thus, in some embodiments, in response to breach of the barrier 24 by the actuator 26 and squeezing of the fluid storage unit 20, the fluid 28 may flow from the reservoir 22 into the lumen of the catheter hub 12 and the catheter assembly may be primed. In these and other embodiments, the fluid storage unit 20 may be compressible towards an axis 30 of the fluid storage unit aligned with the actuator 26 and/or the fluid storage unit 20 may be compressible towards another axis 32 of the fluid storage unit 20 perpendicular to the actuator 26. In some embodiments, the barrier 24 may be breached by the actuator 26 in response to a proximal portion of the fluid storage unit 20 and a distal end of the fluid storage unit 20 being brought closer together, as illustrated, for example, in FIG. 2B. In some embodiments, the fluid storage unit 20 may be constructed of a flexible or semi-flexible material, which may facilitate compression and/or movement of the fluid storage unit 20. For example, the fluid storage unit 20 may be constructed of plastic.

In some embodiments, the proximal portion of the fluid storage unit 20 and the distal end of the fluid storage unit 20 may brought closer together in response to the proximal portion of the fluid storage unit 20 being pushed towards the adapter 18 and/or the adapter 18 being pushed towards the proximal portion of the fluid storage unit 20.

In some embodiments, the distal end of the fluid storage unit 20 may include a luer adapter 34 or another coupling mechanism, which may allow the distal end of the fluid storage unit 20 to be coupled to the adapter 18. In some embodiments, the luer adapter 34 may prevent leakage and/or ingress of microorganisms. For example, the distal end of the fluid storage unit 20 may include a male luer, which may be coupled to a female luer of the adapter 18. Alternatively, for example, the distal end of the fluid storage unit 20 may include a female luer, which may be coupled to a male luer of the adapter 18. In some embodiments, after the priming of the catheter assembly, the fluid storage unit 20 may be removed from the catheter assembly and/or connected to an infusion device, such as, for example, an IV drip chamber. In some embodiments, the fluid storage unit 20 may be uncoupled and removed from the adapter 18 and replaced with another fluid storage unit 20, which may facilitate additional flushing. In some embodiments, additional flushing may follow catheter 15 insertion failure.

In some embodiments, the actuator 26 may include a hollow spike, which may facilitate breach of the barrier 24. In other embodiments, the actuator 26 may be blunt. In some embodiments, the barrier 24 may include a membrane, as illustrated, for example, in FIGS. 2A-2B. In some embodiments, membrane may be hydrophobic. In some embodiments, the barrier 24 may include a septum or another suitable barrier element.

In some embodiments, the fluid storage unit 20 may be pre-attached to the catheter assembly and/or pre-filled with the fluid 28 such that connection or disconnection of the fluid storage unit 20 to the catheter assembly, which may increase a risk of contamination, is avoided. In some embodiments, the catheter system 10 may be included in a kit, which may include the fluid storage unit 20 pre-attached to the catheter assembly and pre-filled with the fluid 28. In some embodiments, priming of the catheter assembly via the fluid storage unit 20 may facilitate mobility of the patient after the catheterization and/or flexibility of the clinician during catheterization, as opposed to, for example, priming via the IV drip-chamber or pre-filled syringe.

Figure 3A:
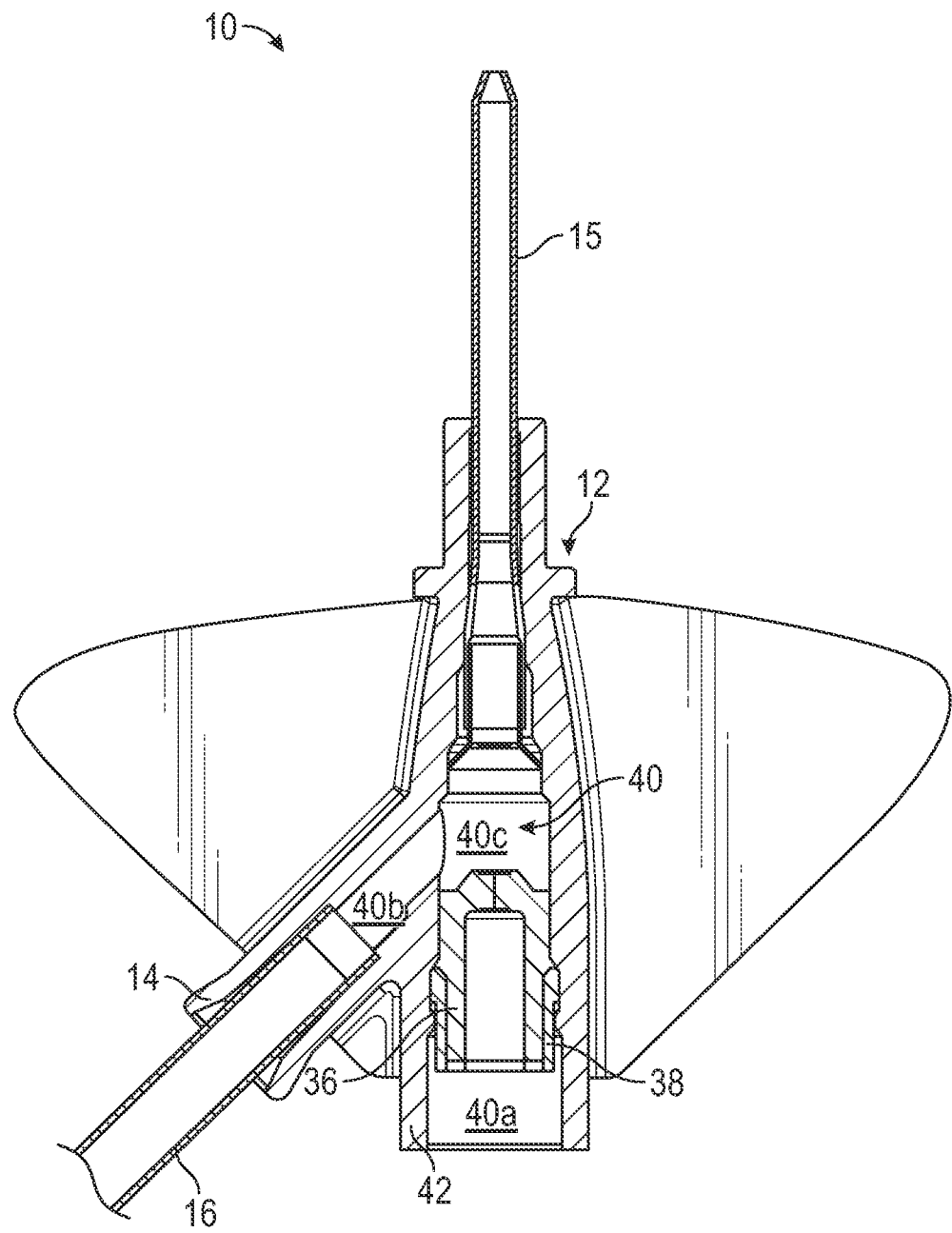
FIG. 3A is a cross-sectional view of an example catheter hub of the catheter system of FIG. 1, according to some embodiments.

Referring now to FIG. 3A, in some embodiments, the catheter hub 12 may include a septum 36 and/or a septum housing 38. It is contemplated that the septum 36 may include any number of types of septa and may be positioned at various locations with respect to the catheter hub 12. In some embodiments, the septum 36 may be disposed within the lumen 40 of the catheter hub 12. In some embodiments, the septum 36 may be at least partially disposed within the septum housing 38 and configured to at least substantially seal the lumen 40 of the catheter hub 12. In some embodiments, the septum housing 38 may prevent dislodgement or destabilization of the septum 36, thereby preventing leakage of fluid from the lumen of the catheter hub 12.

In these and other embodiments, the lumen 40 of the catheter hub 12 may include a first lumen 40a and/or a second lumen 40b. In some embodiments, the proximal end of the catheter hub 12 may form the first lumen 40a and/or the side port 14 may form the second lumen 40b. In some embodiments, the first and second lumens 40a, 40b may join at a common lumen 40c. In some embodiments, the first lumen 40a may be generally aligned with the common lumen 40c. In some embodiments, the septum 36 and/or the septum housing 38 may be disposed in the first lumen 24.

In some embodiments, the second lumen 40b of the catheter hub 12 may be coupled with the fluid storage unit 20 via the extension tube 16 that may extend from the side port 14 of the catheter hub 12. In some embodiments, the extension tube 16 may extend from the proximal end of the catheter hub 12 or another port of the catheter assembly. In some embodiments, the extension tube 16 may include a clamp.

Figure 3B:
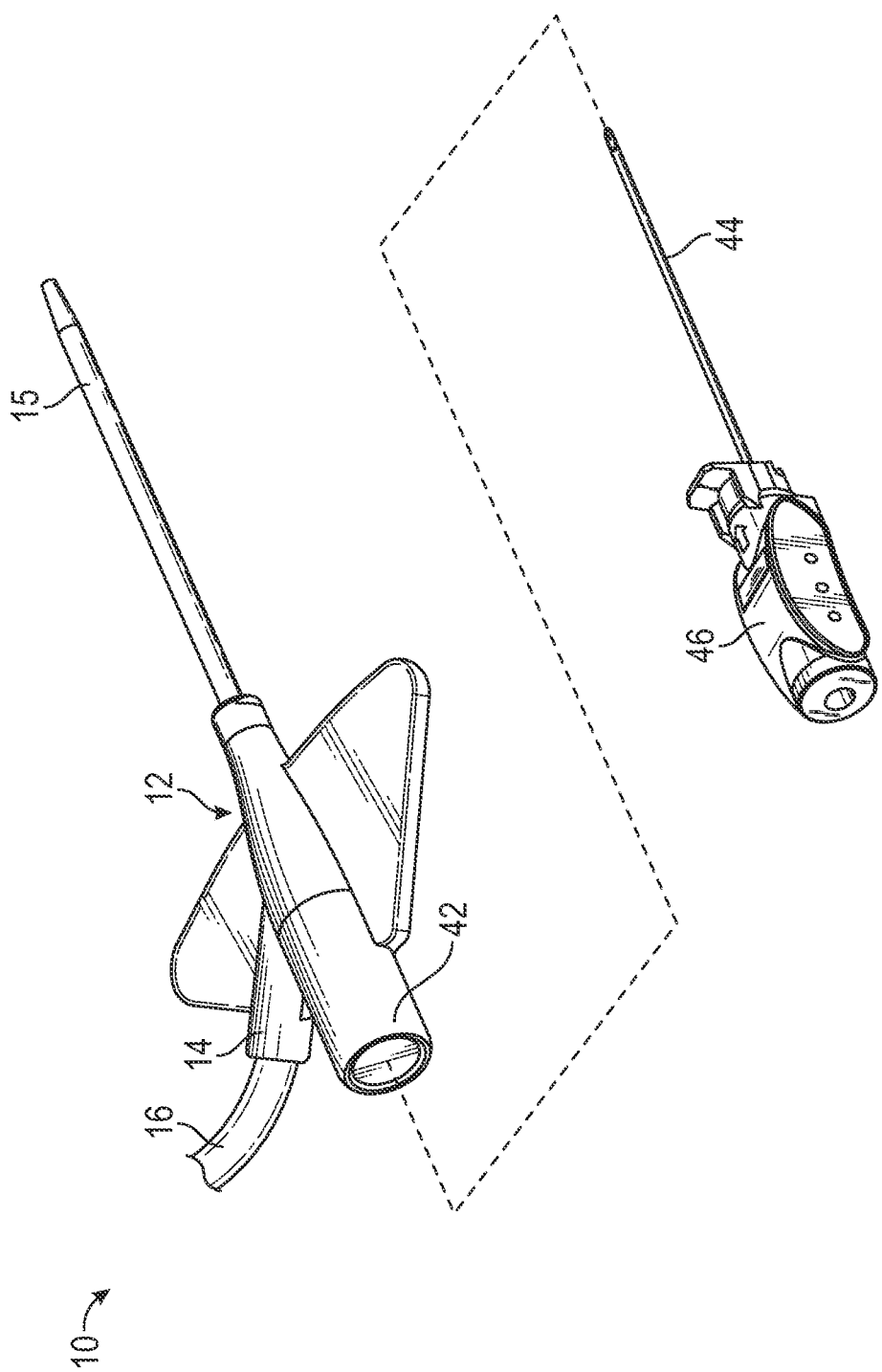
FIG. 3B is an upper perspective view of an example needle hub configured to be coupled with the catheter hub of FIG. 3A, according to some embodiments.
Figure 4:
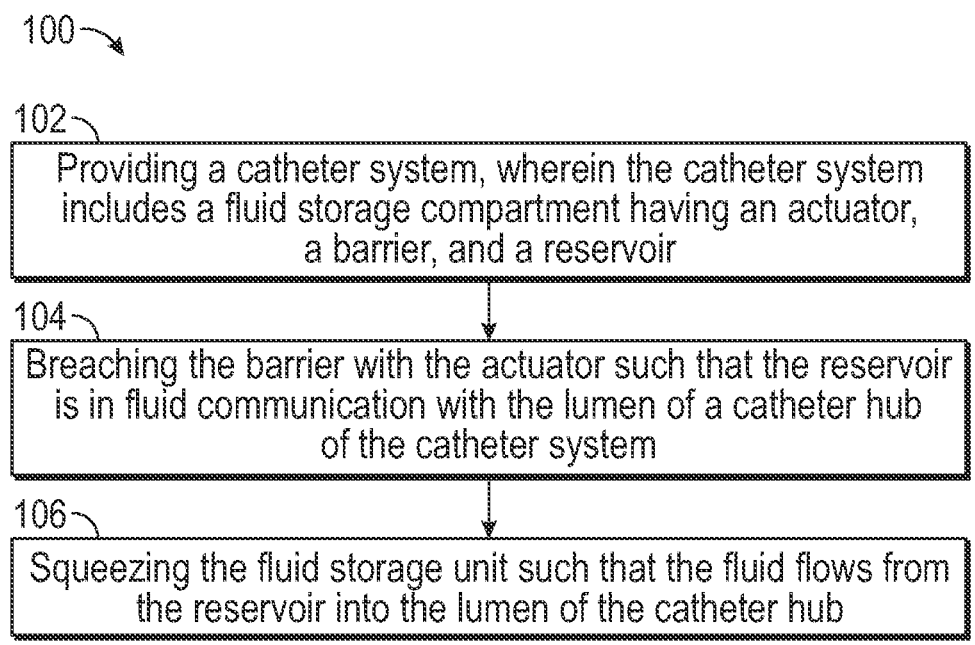
FIG. 4 is a block diagram illustrating an example method of priming a catheter assembly, according to some embodiments.

Referring now to FIG. 3B, in some embodiments, an introducer needle 44 of the catheter assembly may be withdrawn through the catheter hub 12 after insertion of the catheter 15 into the vasculature of the patient. In the closed IV catheter assembly, when the introducer needle is withdrawn through the catheter hub 12, the first lumen 24, which may correspond to a "needle channel," may be closed off by the septum from an external environment surrounding the catheter hub 12. Thus, the septum may at least substantially seal the proximal end of the catheter hub 12 and prevent fluid from exiting the catheter hub 12 through the proximal end of the catheter hub 12. In some embodiments, the fluid pathway of the catheter assembly 14 during fluid priming and/or infusion may extend through the side port 14 and not the proximal end of the catheter hub 12.

In some embodiments, a method 100 of priming a catheter assembly may begin at block 102. At block 102, a catheter system may be provided. In some embodiments, the catheter system may include one or more of the following: a catheter hub, a catheter, an extension tube, an adapter, a fluid storage compartment, and fluid. In some embodiments, the fluid storage compartment may include one or more of the following: an actuator, a barrier, and a reservoir. In some embodiments, the catheter system, the catheter hub, the catheter, the extension tube, the adapter, the fluid storage compartment, and the fluid may include or correspond to the catheter system 10, the catheter hub 12, the catheter 15, the extension tube 16, the adapter 18, the fluid storage compartment 20, and the fluid 28, respectively, described with respect to any of the previous FIGS. 1-3. In some embodiments, the Block 102 may be followed by block 104.

At block 104, the barrier may be breached with the actuator such that the reservoir is in fluid communication with the lumen of the catheter hub. Block 104 may be followed by block 106.

At block 106, the fluid storage unit may be squeezed such that the fluid flows from the reservoir into the lumen of the catheter hub. In some embodiments, the fluid storage may be squeezed by a clinician. In some embodiments, breaching the barrier with the actuator includes bringing a proximal portion of the fluid storage unit and a distal end of the fluid storage unit closer together. In some embodiments, after the priming of the catheter assembly, the fluid storage unit may be removed from the catheter assembly.

Although illustrated as discrete blocks, various blocks may be divided into additional blocks, combined into fewer blocks, or eliminated, depending on the desired implementation. For example, block 106 may be eliminated. In some embodiments, in response to breach of the barrier, the fluid may flow out of the fluid storage unit and through the catheter assembly, priming the catheter assembly.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

The invention claimed is:

1. A catheter system, comprising:
   a catheter assembly, comprising:
      a catheter hub having a distal end, a proximal end, a lumen extending between the distal end and the proximal end, and a side port;
      a catheter extending distally from the distal end of the catheter hub;
      an extension tube having a distal end and a proximal end, wherein the distal end of the extension tube is fixed within the side port; and
      an adapter coupled to the proximal end of the extension tube; and
   a fluid storage unit coupled to the adapter, wherein the fluid storage unit includes a compressible reservoir, a barrier coupled to the compressible reservoir, and a hollow spike aligned with the barrier, wherein the compressible reservoir contains fluid and is entirely disposed on a first side of the barrier, wherein a longitudinal axis of the compressible reservoir is aligned with the hollow spike, wherein the hollow spike in fluid communication with the lumen of the catheter hub is configured to breach the barrier, wherein in response to squeezing of the compressible reservoir that is entirely disposed on the first side of the barrier, the fluid passes from the first side of the barrier to a second side of the barrier.

2. The catheter system of claim 1, wherein the adapter includes a Y-adapter.

3. The catheter system of claim 1, wherein a distal end of the fluid storage unit includes a luer adapter directly coupled to the adapter.

4. The catheter system of claim 1, wherein the barrier includes a septum.

5. The catheter system of claim 1, wherein the barrier includes a membrane.

6. The catheter system of claim 5, wherein the membrane is hydrophobic.

7. The catheter system of claim 1, wherein in response to compression of the compressible reservoir on the first side of the barrier towards an axis of the fluid storage unit aligned with the longitudinal axis of the compressible reservoir aligned with the hollow spike, the hollow spike breaches the barrier such that the fluid passes from the first side of the barrier to the second side of the barrier and the compressible reservoir is in fluid communication with the lumen of the catheter hub.

8. The catheter system of claim 1, wherein in response to compression of the compressible reservoir on the first side of the barrier towards an axis of the fluid storage unit perpendicular to the longitudinal axis of the compressible reservoir aligned with the hollow spike, the hollow spike breaches the barrier such that the fluid passes from the first side of the barrier to the second side of the barrier and the compressible reservoir is in fluid communication with the lumen of the catheter hub.

9. A method of priming a catheter assembly, comprising:
compressing a compressible reservoir of a fluid storage unit coupled to an adapter of a catheter assembly, wherein the catheter assembly comprises:
a catheter hub having a distal end, a proximal end, a lumen extending between the distal end and the proximal end, and a side port;
a catheter extending distally from the distal end of the catheter hub;
an extension tube having a distal end and a proximal end, wherein the distal end of the extension tube is coupled to the side port; and
the adapter coupled to the proximal end of the extension tube;
wherein the fluid storage unit includes the compressible reservoir, a barrier, and a hollow spike aligned with the barrier, wherein the compressible reservoir contains fluid and is entirely disposed on a first side of the barrier, wherein a longitudinal axis of the compressible reservoir is aligned with the hollow spike, wherein in response to compression of the compressible reservoir that is entirely disposed on the first side of the barrier, the fluid passes from the first side of the barrier to a second side of the barrier and the compressible reservoir is in fluid communication with the lumen of the catheter hub;
breaching the barrier with the hollow spike in response to compressing the compressible reservoir; and
after compressing the compressible reservoir of the fluid storage unit coupled to the adapter, inserting the catheter of the catheter assembly into vasculature.

10. The method of claim 9, wherein the adapter comprises a first port and a second port, wherein the proximal end of the extension tube is coupled to the first port.

11. The method of claim 9, wherein a distal end of the fluid storage unit includes a luer adapter.

12. The method of claim 9, wherein the barrier includes a septum or a membrane.

13. The method of claim 9, wherein compressing the compressible reservoir of the fluid storage unit coupled to the adapter comprises compressing the compressible reservoir towards an axis of the fluid storage unit aligned with the longitudinal axis of the compressible reservoir aligned with the hollow spike.

14. The method of claim 9, wherein compressing the compressible reservoir of the fluid storage unit coupled to the adapter comprises compressing the compressible reservoir towards an axis of the fluid storage unit perpendicular to the longitudinal axis of the compressible reservoir aligned with the hollow spike.

15. The method of claim 9, wherein compressing the compressible reservoir of the fluid storage unit coupled to the adapter of the catheter assembly comprises squeezing by a clinician of the compressible reservoir entirely disposed on the first side of the barrier.

16. The method of claim 9, wherein the distal end of the extension tube is fixed within the side port.

\* \* \* \* \*